United States Patent [19]

Boeke

[11] 4,018,513
[45] Apr. 19, 1977

[54] OPTICAL WINDOW USED IN DEVICE FOR MONITORING CLARITY OF A FLUID

[76] Inventor: Jan Boeke, P.O. Box 2511, Chapel Hill, N.C. 27514

[22] Filed: Mar. 26, 1976

[21] Appl. No.: 670,555

Related U.S. Application Data

[62] Division of Ser. No. 455,558, March 28, 1974, Pat. No. 3,954,342.

[52] U.S. Cl. ............................. 350/319; 350/63; 350/96 B; 350/311
[51] Int. Cl.² ............................. G01N 21/12
[58] Field of Search ............ 350/319, 311, 61, 63; 356/208, 207, 206, 205; 256/227, 565, 575; 251/255

[56] References Cited

UNITED STATES PATENTS

| 1,999,639 | 4/1935 | Rosenberger | 350/105 |
| 3,562,795 | 7/1975 | Frank | 350/105 |

*Primary Examiner*—John K. Corbin
*Assistant Examiner*—B. Wm. de los Reyes
*Attorney, Agent, or Firm*—Connolly and Hutz

[57] ABSTRACT

The measurement and reference photocells of an optical detector for a smokestack are disposed adjacent each other on one side of the stack. The measurement photocell and its light-accepting window are disposed on the opposite side of the stack from the light source and the reference photocell has its light-accepting window disposed closely adjacent the light source. A light conducting conduit extends through or around the smokestack within a casing which shields and conducts the light directly emitted from the light source to the reference photocell. Purging air flows within the casing and outwardly through the windows to prevent soot from collecting on them, and the windows are shielded by perforated covers which equalize the flow of air over their entire area and maximize velocities for a given air flow. Wire mesh screens of rounded wire generate a Coanda effect around their outer contours which helps prevent soot from settling within the openings. The reference photocell is connected in a reference integrating circuit having a predetermined switching parameter. The measurement photocell is also connected in a measurement integrating circuit having readout means. The switching means for the reference integrating circuit is connected to the measurement integrating circuit to trip it off after a predetermined amount of light has been detected by the reference integrating circuit. The readout is a measure of the amount of light received by the measurement photocell while the predetermined amount of light is received by the reference photocell and accordingly represents the clarity of the fluid. The integrating circuits may be capacitive networks with voltage comparator and operational amplifiers, and the switching means for operating relays to obtain a readout from the measurement integrating circuit and to reset both of the integrating circuits is effectively provided by a silicon controlled rectifier.

7 Claims, 3 Drawing Figures

OPTICAL WINDOW USED IN DEVICE FOR MONITORING CLARITY OF A FLUID

CROSS-REFERENCE TO RELATED APPLICATIONS

This is a division of Ser. No. 455,558, filed Mar. 28, 1974, now U.S. Pat. No. 3,954,342.

BACKGROUND OF THE INVENTION

Meters capable of determining the clarity or opacity of fluids are highly useful for monitoring fluids such as air, water or process fluids, such as lubricating oil. Various electronic instruments have been proposed for this service, such as described in U.S. Pat. No. 3,617,756, but they are relatively complicated and expensive and subject to malfunctions when operated in a contaminating environment. An object of this invention is to provide a relatively simple, economical and efficient optical device for monitoring the clarity or opacity of the fluid and it more particularly relates to such a device for use as a smoke detector on a smokestack.

SUMMARY

In accordance with this invention a light-accepting window of a measurement photosensitive element is disposed in the path of a light beam projected across the fluid. The light-accepting window of a reference photosensitive element is disposed closely adjacent the source of light, to conduct the light substantially directly emitted from the source to the reference photosensitive element. The light source may be an electric lamp or the light may be conducted by a light pipe or fiber optics from a lamp located in the same box as the photocells (using light shielding), to the location in the stack opposite the measurement window. The reference photosensitive element is connected to an integrating electric circuit which trips a switch connected to the measurement integrating network (incorporating the measurement photosensitive element) when a predetermined amount of light has impinged upon the reference photosensitive element. Readout means on the measurement integrating circuit indicates the relative amount of light impinging on the measurement photosensitive element during the period required for the same amount of light to impinge upon the reference photosensitive element, thus providing an indication of the clarity of the fluid. The photosensitive elements may be disposed closely adjacent each other to cancel out the effects of ambient physical conditions, and a light conduit then conducts the light from adjacent the source to the reference photosensitive element. The device may be enclosed in a casing through which purging fluid is circulated outwardly through the windows to maintain them clear. These windows may be shielded by perforated covers to maximize and equalize the velocity of the issuing fluid over the entire area of the windows. Screens of rounded wire mesh are particularly effective in preventing the settling of contaminating substances within the pores of the covers.

BRIEF DESCRIPTION OF THE DRAWING

Novel features and advantages of the present invention in addition to those mentioned above will become apparent to one skilled in the art from a reading of the following detailed description in conjunction with the accompanying drawings wherein similar reference characters refer to similar parts and in which.

DESCRIPTION OF THE PREFERRED EMBODIMENTS

Figure 1:
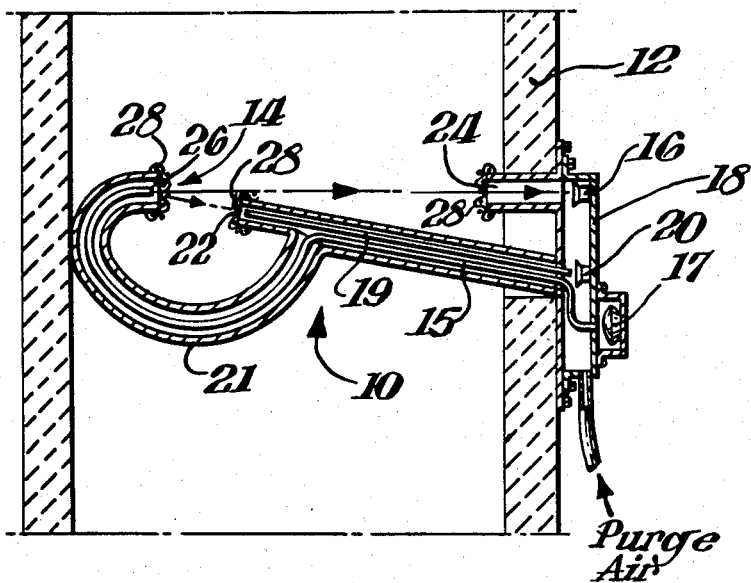
FIG. 1 is a diametrical cross-sectional view in elevation of one embodiment of this invention installed on a smokestack.

In accordance with this invention a smoke detector 10 is mounted on a smokestack 12. Smoke detector 10 includes a light source 14 mounted on one side of smokestack 12 opposite from a measurement photosensitive element 16 disposed within a casing 18. Casing 18 is for example made of stainless steel or heat resistant aluminum. Reference photosensitive element 20 is mounted in casing 18 adjacent measurement photosensitive element 16 to cancel out any differential in ambient physical conditions, such as temperature. The light-accepting window 22 associated with reference photocell 20 is disposed closely adjacent light source 14 for providing a signal indicative of the amount of light directly emitted from light source 14, whereas, light-accepting window 24 associated with measurement photocell 16 is disposed across the interior of the smokestack from a source 14 to cause it to provide a signal indicative of the amount of light transmitted through the smoke within stack 12.

Light-accepting windows 22 and 24 as well as light-transmitting window 26 in casing 21 adjacent light source 14 are shielded by perforated covers 28 which maximize the velocities of the fluid air streams and equalize them over the area of the covers. This prevents contaminating particles such as soot from settling out within the perforations. Light source 14 includes, for example, a single filament automobile sealed beam headlamp 17 (twelve volt) connected by light pipe or fiber optics 15 to carry the light from a light-shielded lamp 17 in the photocell-box 18 to a location in the stack opposite the measurement-window. The light pipe thus creates a light source which is better capable of withstanding high temperatures or corrosive conditions (especially in liquids) than a direct lamp. Light-accepting window 22 is brought closely adjacent light source 14 by disposing another light-conducting element 19, such as a glass rod, between reference photocell 20 and light source 14 within casing 18. There should be no light leakage between the two light circuits in the same conduit 21, which is prevented by suitable shielding (not shown).

Covers 28 are effectively provided by rounded stainless steel wire screens of standard square mesh. A 400 to 625 mesh per inch size is considered highly effective and it, for example, provides an open area which is approximately 32 to 25 percent of the overall area. Covers 28 may also be effectively provided by porous filter glass covers made from porous sintered glass of the separatory type used for filters in chemical laboratories. The filter aspect of porous glass cover 28 may be augmented by incorporating optical filtering media for filtering out longer wave lengths to obtain a more accurate representation of obstruction by smaller particles. The speed with which air can be blown through the light transmitting openings of an air-purged smoke recorder is limited, since otherwise smoke is blown out of the optical path of the measurement. But at low purging air speeds, the updraft in the stack causes turbulence at the optical exit, and a counter-current along the bottom of the exit tube may carry smoke inwardly towards the optical elements. This is eliminated by using the finely perforated cover over the light exit. At a low purge-air flow, each of the narrow openings in the porous cover or screen acts like an orifice with a high relative (to the path diameter) air velocity which keeps smoke out. Moreover, the "Coanda" effect will make this air flow follow the contour of the wire outside, keeping soot from settling. Van Nostrand's Scientific Encyclopedia, Fourth Edition describes the Coanda effect. The pressure drop along the path through the mesh opening (which increases as the square of the flow rate.) will also cause air to flow at about the same rate through the mesh at the bottom as well as the top, regardless of stack updraft, and nowhere will smoke be entrained inside.

Looking at the light source 14, through their wire-mesh window covers 28 are two photocells: the measurement cell 16 at the opposite wall of the stack, and the reference photocell 20 which receives its light either through a clear air path (if rectilinear) or through a light-pipe (if bent) from only a small distance from the light source — a distance negligibly small when compared to the stack diameter. Both light-entrances or windows 22 and 24 to the photocells are also perforated or screened and air-purged. In this way, the reference cell 20 looks through the same number of optical window as the measurement cell 16; and all the optical windows are similarly exposed to fouling conditions.

Figure 2:
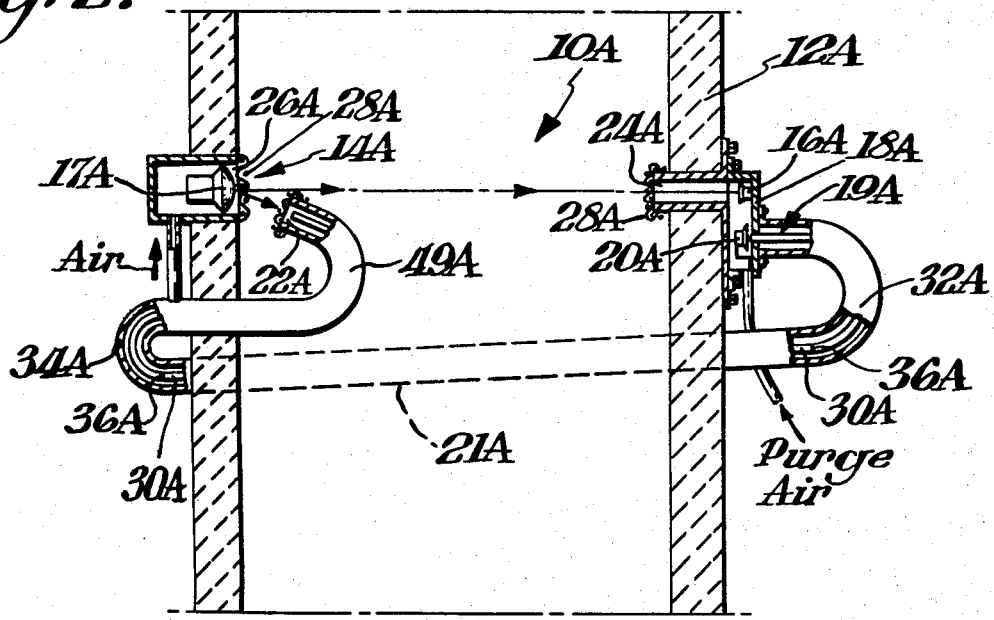
FIG. 2 is another diametrical cross-sectional view in elevation of another embodiment of this invention.

The light-pipe can go through the middle of the stack as shown in FIG. 1 or it can be bent around its outside as shown in FIG. 2.

Figure 3:
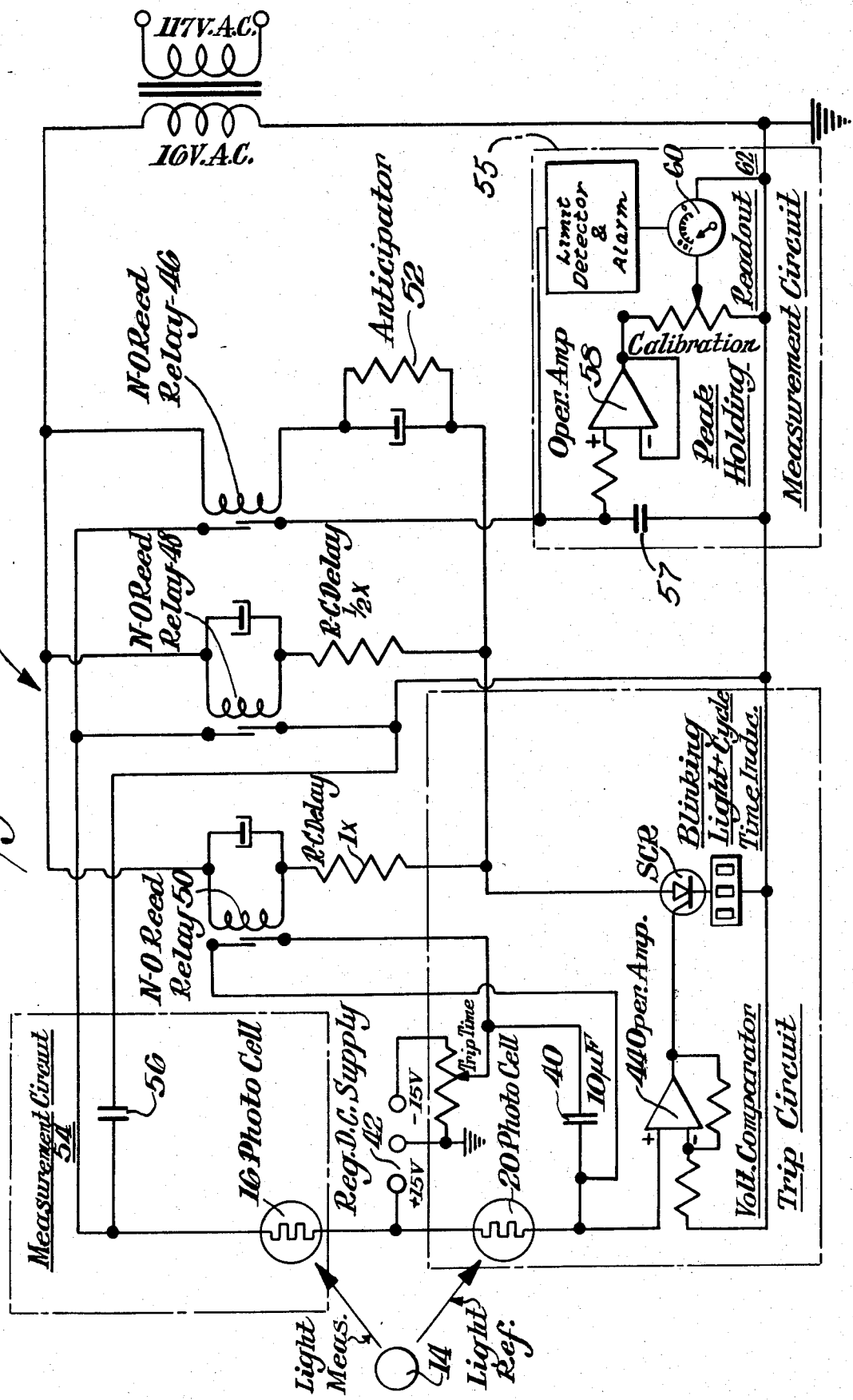
FIG. 3 is a schematic electrical diagram of the embodiment shown in FIGS. 1 and 2.

FIG. 3 shows the electrical diagram for smoke detector 10 which utilizes resistive photocells (e.g. CdS or CdSe photoresistors) in an R-C circuit, which fills a capacitor with charge from a constant voltage source, through a resistor, here the photoresistor. The reference cell 20 will, at the same light-capture, always take the same time to charge the capacitor to the same trip-voltage. When the trip-voltage is reached, it trips a relay-function which quickly discharges the capacitor, and so restarts the charging cycle. If the photocell characteristics do not change, the duration of this cycle is solely dependent on the amount of light captured by the reference cell 20, both cells will have the same temperature and hence the same cell characteristics, thus cancelling out ambient physical effects.

The measurement cell 16 is placed in a similar R-C-circuit, but instead of charging the measurement capacitor until a fixed voltage level is reached, as with the reference circuit, it is the trip-function of the reference cell which also discharges the measurement capacitor. However, if the measurement cell always receives the same (or proportionally the same) amount of light as the reference cell, the measurement capacitor will always charge to the same total voltage. Even if the candlepower of the light bulb changes or the optical windows foul up, total or summed charging voltage of the measurement capacitor will stay the same because the changes in light captured are the same for both photocells. All that such a change in light will do, is to change the cycle-time of the trip-function. Thus, the cycle-time becomes a measurement of drop-off of light-intensity due to light-bulb-aging or window-foulup.

However, if in such a set-up smoke in the stack attenuates the light received by the measurement-photocell, the charging-voltage of the measurement capacitor does go down. A peak-holding voltmeter on this capacitor indicates opacity of the stack gases. Clear stack gases push the pointer to the end of the scale for zero opacity. Smaller pointer excursions will indicate increasing opacities due to increasing smoke. An alarm function can be set to go off if pointer excursions go down below a certain scale indication for opacity. Since any failure in the electrical or optical circuits of the instrument would lead to the pointer going down all the way, this would also sound the alarm. The instrument is, therefore, intrinsically fail-safe, which means that the owner of the stack can never be polluting the air with smoke unawares, if his instrument fails. He would be alerted to either smoke or to an instrument breakdown. In the latter case the time-cycle indication would go to infinitely long time cycles and hence indicate the cause of the alarm.

The system of charging the capacitor over a period of time over which light-signals are received from the light-bulb, is an integrator, which inherently has the tendency to smooth out small variations in smoke density or other sources of "noise" in the electrical part of the system. Also, the level of illumination of the photocell can now be extremely low, since with enough time, sufficient signal will be collected for a reliable readout. This again means that the optical windows could foul up to a large degree before the system would become inoperable.

With other instruments, window foul-up causes a shift in recording zero (separately indicated every hour) and hence, due to the logarithmic character of the transmittance-scale, an error in transmittance reading, especially at large zero-shifts. In this invention, meter readings are totally unaffected by window-foulup and no zero-shift takes place. As a matter of fact: this characteristic of this invention, combined with the wire-screen windows, could well make maintenance superfluous, until the light-bulb burns out. The bulb has a life span better than 10,000 hours, i.e. over one year life-span.

Operation

The electrical diagram shown in FIG. 3 operates in the following manner. The reference light 14 in the timing circuit falls on a photo resistor 20 which becomes more conductive the more light falls on it. Capacitor 40, which is marked 10 microfarad, is charged up through reference photo resistor 20 by regulated D.C. supply 42. The charge goes from −15 volt toward +15 volt. Continuously, the operational amplifier 44, which acts as a voltage comparator compares the charge value to the middle zero volts of ground. When the charge of capacitor 40 passes through this zero volts value, voltage comparator 44 starts to amplify a positive voltage which immediately trips the S.C.R. (silicon controlled rectifier). The S.C.R. will now pass the positive peaks of an A.C. source. The resulting pulsating D.C. current energizes three normally-open reed relays 46, 48 and 50. The first relay to close, because of an anticipating circuit 52 in its feed line, is relay 46 which connects measurement circuit 54 to a measurement capacitor 56 charged by measurement photo resistor 16.

The second relay 48 to close, because of its short time R-C delay circuit, discharges measurement capacitor 56 back to zero volts after the first relay 46 has opened again. The third reed relay 50, last to close because of a longer time R-C delay circuit, discharges the reference capacitor 40. Upon dissipation of the charge voltage on reference capacitor 40, voltage comparator 44 stops its positive input to S.C.R. and thus de-energizes all the relays. This means that the trip cycle can start anew. Now especially considering the measurement circuit 54, the measuring light falling on the measurement photo resistor 16 determines the rate at which the measurement capacitor 56 is being charged up from the regulated D.C. supply. The voltage resulting from this charge is periodically transferred to a summing or totalizing capacitor by way of the first mentioned reed relay 46. Operational amplifier 58 in a high input impedance mode transfers the charge value of the summing or totalizing capacitor to the read out meter 60 and/or to record 62.

Smoke detector 10A shown in FIG. 2 has light-conducting casing 21A disposed around the outside of smokestack 12A instead of passing through it. Only a small portion 49A of gooseneck shape is disposed within smokestack 12A and is, therefore, made of a heat resistant metal such as stainless steel or aluminum. The remaining portions of casing 21A are, for example, made of an opaque plastic such as an opaque nylon tubing. Lamp 17A is similar to lamp 17 but directly provides light source 14A because it is disposed substantially outside of the heat of the stack and its corrosiveness.

The relatively straight portion 30A of the light conduit 19A is, for example, made of an acrylic plastic having highly efficient light-transmitting characteristics. Relatively bent portions 32A and 34A are made of glass fiber optics connected at joints 36A to straight light conducting conduit 30A by suitable optically clear cement, such as Canada balsam cement. Other than the disposition of casing 21A and light-conducting conduit portions 30A and 32A outside of the smokestack, the other aspects of detector 10A are the same or substantially similar to smoke detector 10, in which light-conducting casing 21 projects inside the smokestack.

I claim:

1. A light-transmitting window for a smoke detector having an air purged casing comprising a light-transmitting opening in said casing, and a finely perforated cover over said opening which equalizes and maximizes the velocities of the purging airstreams flowing outwardly through said perforation whereby their obstruction is reduced.

2. A light-transmitting window as set forth in claim 1 wherein said perforated cover is comprised of screen mesh.

3. A light tramsitting window as set forth in claim 1 wherein said screen mesh is comprised of round wire.

4. A light-transmitting window as set forth in claim 3 wherein said perforated cover is comprised of porous glass.

5. A light-transmitting window as set forth in claim 4 wherein said porous glass is comprised of separatory filter type glass.

6. A light-transmitting window as set forth in claim 4 wherein said glass in said porous glass includes an optical filtering medium.

7. A light-tramsitting window as set forth in claim 6 wherein said porous glass is also of the separatory filter type.

* * * * *